United States Patent [19]

Schapira et al.

[11] Patent Number: 6,080,700
[45] Date of Patent: Jun. 27, 2000

[54] METHOD AND ETHEPHON-BASED COMPOSITION FOR CONTROLLING PLANT GROWTH

[75] Inventors: Joseph Schapira, Paris; Jacques Vincent, Mareil Marly; Jacques Schild, Gennevilliers; Isabelle Maillet, Paris, all of France

[73] Assignee: CFPI Agro, Gennevilliers, France

[21] Appl. No.: 08/875,254

[22] PCT Filed: Jan. 4, 1996

[86] PCT No.: PCT/FR96/00018

§ 371 Date: Sep. 24, 1997

§ 102(e) Date: Sep. 24, 1997

[87] PCT Pub. No.: WO96/20603

PCT Pub. Date: Jul. 11, 1996

[30] Foreign Application Priority Data

Jan. 6, 1995 [FR] France .................................. 95 00125

[51] Int. Cl.⁷ .................................................. A01N 57/00

[52] U.S. Cl. ............................................. 504/127; 504/128
[58] Field of Search ............................ 514/274; 423/235; 504/127, 128

[56] References Cited

U.S. PATENT DOCUMENTS

| | | | |
|---|---|---|---|
| 5,145,856 | 9/1992 | Clough et al. | 514/274 |
| 5,441,713 | 8/1995 | Dublin et al. | 423/235 |

*Primary Examiner*—S. Mark Clardy
*Assistant Examiner*—Alton Pryor
*Attorney, Agent, or Firm*—Jones & Askew, LLP

[57] ABSTRACT

Ethephon-based composition for the regulation of plant growth containing in addition to ethephon, at least one product or adjuvant the chemical structure of which contains at least two acid functions selected from carboxylic acid type of formula (—COOH) and phosphonic acid type of formula (—$PO_3H_2$), at least one of these acid functions being the (—$PO_3H_2$) function.

11 Claims, No Drawings

METHOD AND ETHEPHON-BASED COMPOSITION FOR CONTROLLING PLANT GROWTH

This application is a 371 of PCT/FR96/00018 filed Jan. 4, 1996.

A subject of the invention is a process for the regulation of plant growth, this process using ethephon.

It also relates to an ethephon-based composition for the regulation of plant growth.

It should be noted that ethephon, or 2-chloroethylphosphonic acid, is a plant growth regulator which is presented in the form of an acid grey solid, melting at about 74–75° C.; its high solubility in water allows it to be handled more conveniently, without isolating it, in the form of a concentrated solution of about 1000 g/l.

It is presumed that its biological activity is linked to the emission of ethylene, outside and/or inside plants and to the fact that it probably triggers an endogenic emission of ethylene in the plant via a cascade effect. As a growth regulator, it can be used to provoke ripening of fruits and vegetables, to reduce the length of stems and straw of cereals, to encourage the axillary or apical budding of certain flowers and to increase the production of latex during the tapping of rubber plants.

Ethephon also encourages the early and uniform opening of ripe cotton boll and provokes the senescence of leaves or even their falling depending on the conditions of the medium, which facilitates harvesting.

Document GB-A-1 505 331 already discloses compositions comprising on one hand a compound providing ethylene and on the other hand a chelating agent.

Moreover, the prior art documents DD-A-237 253 and DD-A-139 063 disclose compositions comprising ethephon and a compound constituted by a hydrocarbonated chain having one carbon atom, bisubstituted by two phosphonic acid functions.

Within the scope of its research directed with a view to making better use of the biological properties of a compound constituted by a hydrocarbonated chain with one carbon atom, bisubstituted by two phosphonic acid functions.

Within the scope of its research directed with a view to making better use of the biological properties of ethephon, in other words obtaining quicker or more intense biological effects for a given quantity of active ingredient, the Applicants had the merit of discovering that this goal could unexpectedly and surprisingly be achieved when ethephon was used in a concomitant fashion with at least one of the substances of a group of products known until now for properties exhibited in technical fields as removed from agriculture as the fluidification of cements, softening and detergent treatment of textiles, the formation of chelating agents with multivalent metals or also the treatment of feed-water for boilers, the chemical structure of these products which can be conveniently designated by the term "adjuvants" being characterized by the presence of at least two acid functions chosen from the group containing acid functions of carboxylic type of formula (—COOH) and those of phosphonic type (—PO$_3$H$_2$), at least one of these acid functions being the (—PO$_3$H$_2$) function, these acid functions being connected by optionally substituted carbon chains defined hereafter.

It follows that the plant growth regulation process according to the invention is characterized in that on the plants to be treated there is used ethephon and at least one product, the chemical structure of which is characterized in that it contains at least two acid functions chosen from the group containing acid functions of carboxylic type of formula (—COOH) and those of phosphonic type (—PO$_3$H$_2$), at least one of these acid functions being the (—PO$_3$H$_2$) function, said product being selected from the group comprising that having the formula

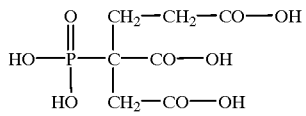

and those in which the acid functions are connected by an organic chain of (—R—O—R) type containing an ether function and in which R represents a linear or branched hydrocarbon chain containing from 2 to 6 carbon atoms and optionally one or more substituents of hydroxyl type (—OH) and/or halogen and/or hydroxyethyl (—CH$_2$—CH$_2$—OH) and/or phenyl (—C$_6$H$_5$) and/or hydroxyphenyl (—C$_6$H$_4$—OH), the two chains R can be identical to or different from each other, and/or an organic chain of (—R—NH—R) type containing a secondary amine function and in which R is defined as above, the two chains R can be identical to or different from each other, and/or an organic chain of

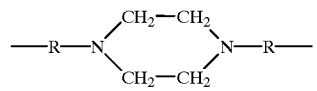

type containing two tertiary amine functions and in which R is defined as above, the two chains R can be identical to or different from each other, and/or by a chain of

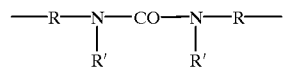

type in which (—R') represents hydrogen or the aforementioned chain R, and/or by an organic chain of

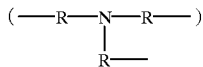

type containing a tertiary amine function in which R is defined as above, the three chains R can be identical to or different from each other.

The composition according to the invention based on ethephon for the regulation of plant growth is characterized in that it contains, in addition to ethephon and, if necessary, the usual constituents of ethephon-based compositions, at least one product or adjuvant the chemical structure of which contains at least two acid functions chosen from the group containing acid functions of carboxylic type of formula (—COOH) and those of phosphonic type (—PO$_3$H$_2$), at least one of these acid functions being the (—PO3H2) function, said product being selected from the group comprising that having the formula

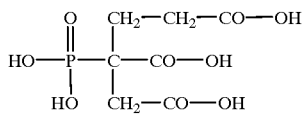

and those in which the acid functions are connected
by an organic chain of (—R—O—R) type containing an ether function and in which R is defined as above, the two chains R can be identical to or different from each other,
and/or an organic chain of (—R—NH—R) type containing a secondary amine function and in which R is defined as above, the two chains R can be identical to or different from each other,
and/or an organic chain of

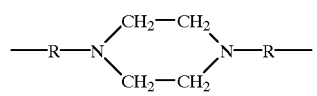

type containing two tertiary amine functions and in which R is defined as above, the two chains R can be identical to or different from each other,
and/or by a chain of

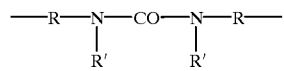

type in which (—R') represents hydrogen or the aforementioned chain R,
and/or by an organic chain of

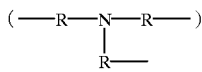

type containing a tertiary amine function in which R is defined as above, the three chains R can be identical to or different from each other, at least one of these acid functions being the (—PO$_3$H$_2$) function.

According to an advantageous implementation of the process and composition according to the invention, the product or adjuvant is characterized in that its chemical structure, which contains at least two acid functions, is represented by one of the general formulae indicated hereafter:

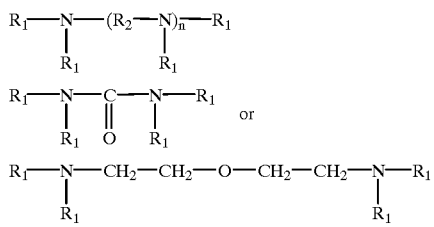

or

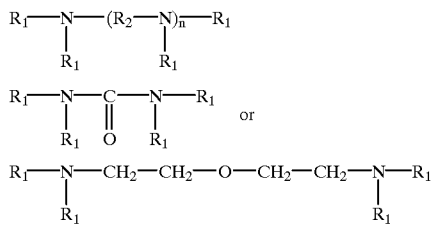

in which n represents an integer from 0 to 4,

R$_2$ represents a linear or branched hydrocarbon group having 2 to 6 carbon atoms, R$_1$ represents, independently at each occurrence, a hydrogen atom, an alkyl chain having 1 to 4 carbon atoms, a phenyl group, a hydroxyphenyl group, a hydroxyalkyl group, an alkylene-phosphonic acid group or one of the five groups represented below:

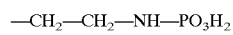

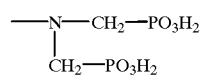

(the number of —CH$_2$COOH groups being at most three)

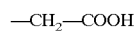

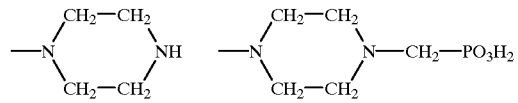

According to another advantageous implementation of the process and composition according to the invention, the product or adjuvant is characterized in that its chemical structure, which contains at least two acid functions, is represented by the formula

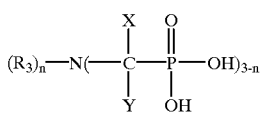

in which n represents an integer equal to 0 or 1,

X and Y represent a hydrogen atom or an alkyl group having 1 to 6 carbon atoms,

R$_3$ represents a hydrogen atom, an aliphatic hydrocarbon group, a halo-substituted aliphatic hydrocarbon group, a hydroxy-substituted aliphatic hydrocarbon group, the —CH$_2$COOH group or the

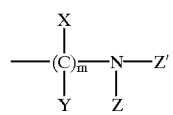

group in which
   m represents an integer from 1 to 6,
   X and Y represent a hydrogen atom or an alkyl group,
   Z represents a hydrogen atom or the

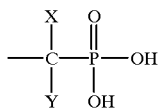

group
   Z' represents Z or the group of formula

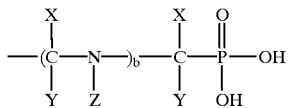

in which b is an integer from 1 to 6.

According to another advantageous implementation of the process and composition according to the invention, the product or adjuvant is characterized in that its chemical structure, which contains at least two acid functions, is represented by the formula

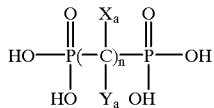

i.e. is constituted by an alkyl-diphosphonic acid,
   $X_a$ being chosen from the groups containing hydrogen or short alkyl groups having 1 to 4 carbon atoms,
   $Y_a$ being chosen from the groups containing hydrogen, a hydroxyl radical, a halogen radical, short alkyl groups containing 1 to 4 carbon atoms,
   n being an integer from 2 to 6.

According to another advantageous implementation of the process and composition according to the invention, the product or adjuvant is characterized in that its chemical structure, which contains at least two acid functions, is represented by the formula

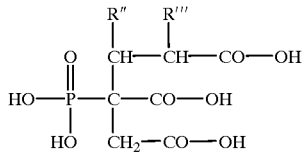

in which
   R" represents hydrogen or a short alkyl chain having 1 to 4 carbon atoms,
   R'" represents hydrogen or a methyl group, the products corresponding to formulae

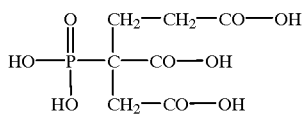

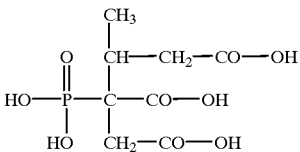

and

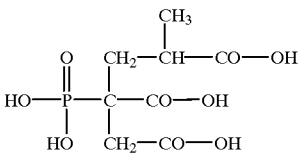

being more particularly preferred.

According to another advantageous implementation of the process and composition according to the invention, the product or adjuvant is characterized in that its chemical structure, which contains at least two acid functions, is represented either by the formula

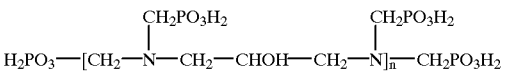

in which n is an integer from 1 to 5, or by the following products:
   1,6-hexylenediamine-N,N,N',N' tetrakis((methylene)-phosphonic) acid,
   ethylenediamine-N,N,N',N'-tetrakis((methylene)-phosphonic) acid,
   diethylenetriamine-N,N,N',N",N"-penta((methylene)-phosphonic) acid,
   nitrilo-N,N,N-tris((methylene)-phosphonic) acid which are particularly preferred.

According to another advantageous implementation of the process and composition according to the invention, the product or adjuvant is characterized in that its chemical structure, which contains at least two acid functions, is represented by one of the formulae

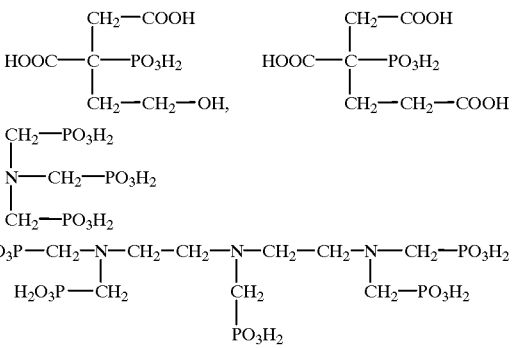

and

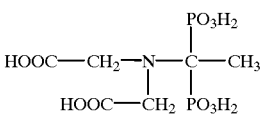

From a more general point of view, the products or adjuvants used in a concomitant fashion with ethephon and identified above are advantageously used in the form of alkaline and/or alkaline-earth salts and/or of salts of amines having 2 to about 18 carbon atoms, these amines being optionally oxyethylenated and/or oxypropylenated, on condition that the pH of the final composition, if it is an aqueous or hydroalcoholic solution, does not exceed 3.

In the composition according to the invention, the ethephon/adjuvant weight ratio is from 10/1 to 1/10, preferably 5/1 to 1/5.

The composition can be presented in the form of an aqueous solution containing one or more wetting agents chosen from the $C_4$ to $C_{18}$ alcohols and/or oxyethylenated and/or oxypropylenated alkylphenols the alcohol function of which at the end of the chain is optionally substituted by an oxyacetic group or a chlorine atom, alkylglucosides, alkanesulphonic and/or alkylarylsulphonic acids, these last-named can be partially or totally neutralized in the form of alkaline and/or alkaline-earth salts and/or of salts of amines having 2 to about 18 carbon atoms, these amines being optionally oxyethylenated and/or oxypropylenated, on condition that the pH of the composition does not exceed 3.

It can also be presented in the form of a powder containing one or more wetting agents chosen from those identified above and an absorbent support which is soluble in water, such as dextrin or maltodextrin, or insoluble in water such as micronized silica, it being understood that, in the latter case, dispersants can be resorted to such as lignosulphonates or polynaphthylmethane-polysulphonates.

Finally, it can be presented in the form of spreadable granules containing one or more wetting agents chosen from those identified above and an absorbent support which is either soluble in water, such as graded dextrin or maltodextrin, or insoluble in water such as graded silicates, in particular Sepiolite®.

The compositions according to the invention can be applied on plants in different ways according to the presentation method.

For example, when these compositions are aqueous solutions, soluble powders, wettable powders or emulsionnable concentrates, dispersible or soluble granules, the plant protection mixture—a term designating the dilution ready to be sprayed on the plants to be treated—is prepared by simply diluting the composition in one part of the water envisaged for the treatment, then by topping up, under stirring, with water to the desired volume.

When these compositions are in the form of spreadable granules, dusting powder or tablets, the composition is spread directly on the soil or placed directly in contact with the plant to be treated, for example in the crown of the pineapple in order to act on its flowering.

According to an advantageous implementation of the process according to the invention, 20 g to 3000 g of ethephon combined with 20 to 5000 g of one or more of the products or adjuvants identified above are applied per hectare according to the cultivation, the physiological stage and the effect sought, the assembly constituted by ethephon and the adjuvant can be diluted in water at the rate of 20 to 3000 liters of water per hectare.

The ethephon can be applied plant by plant and the doses are very weak per plant (rubber plants, pineapples . . . ) or by way of a plant protection mixture or slurry. In the latter case, depending on the application methods, 20 to 3000 liters of water containing 20 to 3000 g of ethephon and 20 to 5000 g of adjuvant can be sprayed per hectare.

The products or adjuvants identified above and used in the process or the composition according to the invention are products known in themselves but for applications extremely distant from those envisaged by the present invention.

In that connection, certain of these products are those described in the Patent U.S. Pat. No. 4,676,832 as substances which allow mortar mixes to remain fluid, i.e. pumpable for longer, these products being constituted by derivatives of methylenephosphonic acid;

certain others are described in the French Patent FR-A-1 342 412 as waterproofing and softening agents for textiles when they have high molecular weights and as complex generators capable of forming chelating compounds with multivalent metallic cations when they have lower molecular weights, the products in question being derivatives of mono-, di- and trialkylenephosphonic acids;

certain others are those described in the French Patent FR-A-1 371 139 as substances which complex metallic ions of aqueous solutions or limit precipitation; these complexing agents aim to improve soaps, shampoos, detergents for textiles or for metals, as well as the polymerization of rubber and plastic materials and are derivatives of amino-tris-alkylidene-phosphonic acid;

certain others are those described in the French Patent FR-A-1 376 001 as deflocculants and dispersants to improve the rheology of dispersed systems, the effectiveness being measured for example by viscosity measurements of kaolin aqueous pastes, the products in question being salts of alkylaminopolyalkylenephosphonic acids and alkyl-poly-alkyleneamine-polyalkylene-phosphonic acids;

certain others are those described in the French Patent FR-A-1 399 074 as substances which are useful as complexing agents of metallic cations such as iron (Fe 111), as deflocculants for drilling fluids for oil wells, as liquefiers for aqueous dispersions of kaolin; these products are salts of aminotri-alklyenephosphonic acids;

certain others are those described in the Patent U.S. Pat. No. 3,336,221 as substances intended to combat scale, in particular from mineral salts of alkaline-earth type, in the presence of the carbonate ion, under the influence of variations of pH, temperature, pressure or the introduction of additional ions capable of forming insoluble compounds with those already present, which hinders heat transfers in the materials scaled in this way and forms sites which favour the development of bacteria; these products, endowed with a threshold effect, i.e. which would be effective at sub-stoichiometric doses relative to the water hardness salts present clearly below a ratio of 1:1 (expressed in moles), are salts of aminotrialkylenephosphonic acids, polyalkylene-amine-polyalkylenephosphonic acids and polyhydroxy-alkyleneamine-polyalkylenephosphonic acids;

certain others are those described in the Patent U.S. Pat. No. 3,368,978 as products which are suitable for improving the detergent properties of certain washing powders, in particular in laundries, concurrently or in combination with tripolyphosphates; they are derivatives of amino-tris-(alkylidenephosphonic acid) acids;

certain others are those described in the French Patent FR-A-1 458 566 as products for the production of washing bars, or auxiliary agents for washing; they are alkylenepolyphosphonic acids and polyalkyleneamine-polyalkylenephosphonic acids;

certain others are those described in the Patent U.S. Pat. No. 3,434,969 as products having several amino-methylene-phosphonic groups, with at least three nitrogenous sites linked by —$CH_2$— bonds ("methylene") capable of inhibiting the formation of scale of carbonate and sulphate type of alkaline-earth ions in the aqueous solutions even at relatively high temperature, exhibiting a threshold effect; these products are alkylamino or polyalkylene-polyamine-(polyalkylenephosphonic) acid salts;

certain others are those described in the Patents U.S. Pat. No. 3,886,204 and U.S. Pat. No. 3,886,205 as products capable of forming complexes with alkaline-earth ions; they are derivatives of alkyl-polycarboxy-phosphonic acid salts;

certain others are those described in the British Patent No. 2 157 279 as products capable of retarding the setting of cement during the injection of hydraulic cement into the soil, or during the mixing of plaster, they are derivatives of alkylamino or polyalkylene-polyamine-(polyalkylenephosphonic) acid salts.

The methods of preparing the products in question are described in the previous patents which have just been described.

As can be noted, the known applications of the products or adjuvants in question in no way allow to forecast the potentializing effect which is manifested when they are used in conjunction with ethephon in accordance with the process or with the composition according to the invention.

This effect is even more unexpected as it is manifested under very different conditions of use, even antagonistic, to those under which the already known properties of said products appear.

In this respect, the agricultural plant protection mixtures based on the composition according to the invention are applied at ambient temperature, whilst the scale inhibitors essentially function during temperature changes of the medium where they are used; in addition, their activity is only noticeable at alkaline pH's, or when they become alkaline (in the best case a pH of 4 according to the French Patent FR-A-1 371 139), while in order to retain the stability of ethephon in the composition according to the present invention, the pH is limited to a maximum of 3.0; similarly, the cements and plasters and the detergents for textiles are alkaline; furthermore, the dispersant properties which characterize certain of these products for example in the kaolin dispersions, have no use within the scope of the present invention, and cannot explain the action of these same products as an "adjuvant" of ethephon since the final aqueous solutions employed in accordance with the invention are homogenous and isotropic solutions.

The compositions according to the invention can be used in all forms which are compatible and acceptable for agronomy.

Concentrated aqueous solutions are particularly convenient to produce, taking into account the good solubility in water, in general, of the different constituents, but gelified aqueous solutions can also be produced in order to avoid splashing during handling or to obtain an anti-drift effect on the plant protection mixture: in this way the possibility of the sprayed product being carried by the wind is limited.

The following can be added to it: antifreeze, emollients, dampness retaining agents, fixing agents for anti-leaching by rain or dew, non-ionic and/or anionic wetting agents, such as, for example, ethyleneglycol, glycerol, fatty alcohols and polyoxyalkylenated alkylphenols, alkylglucosides, as well as alkylsulphonates and alkylarylsulphonates in acid form or in the form of alkaline salts provided that the pH of the formulation does not exceed 3.0.

By adding an aliphatic or aromatic mineral oil, suitably chosen emulsifiers and cosolvants of butylglycol, propyleneglycol, or short fatty alcohols to the composition according to the present invention, micro-emulsions can be produced.

Soluble powders (i.e. powders in which the active ingredients are soluble even if the support is insoluble) can also be produced by absorbing the aqueous solutions of the different constituents on an absorbent support, which can be soluble in water, such as, for example, a dextrin, or which is insoluble such as, for example, silica; in the latter case dispersing agents and wetting agents known to a person skilled in the art are added.

The composition according to the invention can also be presented in the form of spreadable granules by impregnating either a calibrated support produced from reclaimed papers, for example that marketed under the trade mark BIODAC®, or a support constituted by a material based on silicates extracted from deposits and graded, for example that known under the designation SEPIOLITE®.

The invention will be better understood by reference to the non-limitative examples which follow and which relate either to advantageous implementations of the composition according to the invention, or to trials showing the effectiveness of the invention.

1. Ethephon-based Compositions

Three compositions according to the invention are prepared; to do this the solid substances which dissolve in water are dissolved in water; it is also possible to mix the different aqueous solutions of these substances so as to obtain a final aqueous solution having the desired proportions.

The various constituents are weighed beforehand to an accuracy of±0.05 g.

The solution obtained is decanted quantitatively into a calibrated 100 ml flask, then made up to 100 ml and weighed, in this way the density and the content in g/l of the active ingredients can be calculated.

The products or adjuvants used in the three above-mentioned compositions are as follows:

1,2,4-butane-tricarboxylic-2-phosphonic acid the formula of which is

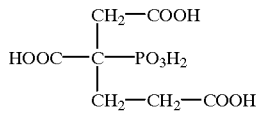

and which is marketed under the trade mark BAYHIBIT AM®, aminotrimethylenephosphonic acid the formula of which is

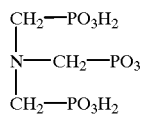

and which is marketed under the trade mark DEQUEST 2000®, diethylenetriamine-pentamethylenephosphonic acid the formula of which is

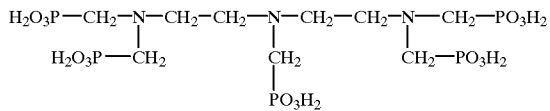

and which is marketed under the trade mark DEQUEST 2060®.

The other constituents of the three above-mentioned compositions are an aqueous solution of ethephon at 1000 g/l and known under the designation BASE A 250 and containing 72% by weight of ethephon, an alkylglucoside known under the trade mark TRITON BG 10 and the function of which is to confer on the plant protection mixture to be applied a certain ability to spread over the treated plants.

The three compositions thus prepared are identified as LAB 695, LAB 696 and LAB 697 respectively.

The proportions of their different constituents and their properties appear in Table I which follows:

TABLE I

| Composition designation | Type of constituents | Weight (g/100 ml) of constituents (content % weight) | Content (g/l) | Remarks |
|---|---|---|---|---|
| Lab 695 | Base A 250 | 14.0 (72%) | 100 | density 1.076 |
| | BAYHIBIT AM | 14.0 (50%) | 70 | easily worked foam with traces of silicon |
| | Triton BG 10 | 1.0 | | |
| | Water | sqf 100 ml (107.6 g) | | |
| Lab 696 | Base A 250 | 14.0 (72%) | 100 | density 1.080 |
| | DEQUEST 2000 | 14.0 (50%) | 70 | easily worked foam with traces of silicon |
| | Triton BG 10 | 1.0 | | |
| | Water | sqf 100 ml (108.0 g) | | |
| Lab 697 | Base A 250 | 14.0 (72%) | 100 | density 1.084 |
| | DEQUEST 2060 | 14.0 (50%) | 70 | easily worked foam with traces of silicon |
| | Triton BG 10 | 1.0 | | |
| | Water | sqf 100 ml (108.4 g) | | |

2. Biological Trials in a Greenhouse

Biological trials in a greenhouse were carried out with the three compositions identified in Example 1.

By way of comparison, a standard solution of ethephon containing 480 g/l of ethephon is used, marketed under the trade mark ETHEREL 48® and which is designated in what follows by CA 152.

In these trials, the ethylenic activity of the three compositions studied is evaluated using a specific test developed on the haricot bean and designated in what follows by "Haricot bean test".

In this test, a batch of haricot plants is treated with the composition to be studied at the half-open trifoliate second leaf stage.

Four hours after treatment:

the plants are topped above the first trifoliate leaf in order to limit the growth of the plants; the first retained trifoliated leaf serves to provide photosynthates;

the limbs of the primary leaves are removed: they are sectioned at their base, leaving only the petiole on the plant.

A batch of untreated control plants is prepared in the same way.

Then, the number of petioles which fall is counted, at intervals of one day and in this way the abscission kinetics induced by each product is established.

The absence of petioles falling from the control plants allows the differences in the abscission kinetics between the treated batches to be verified which well reflects the differences of activity between the applied products.

The plants (Cabri haricot bean variety) are cultivated in pots in greenhouse at a minimal temperature of 13° C.; the day/night cycle is 16/8 hours and the relative humidity is about 70%. The compost is composed of one third sand, one third peat and one third vegetable mould.

The products are sprayed using a spray-line (under a pressure of $1.5 \times 10^5$ Pa); the volume of the plant protection mixture is 1000 1/ha. The dose of ethephon studied is, depending on the trials, 750 or 1000 g per hectare.

For each composition studies, a batch of 20 plants is treated.

All grading is done "blind".

The activity of a regulator is apt to vary as a function of the cultivation conditions. Consequently, the experiments are repeated several times over time in order to validate the results.

a) Series of Trials 1 and 2

In these trials 1 and 2, the ethylenic activity of compositions LAB 695, LAB 696 and LAB 697 is compared to that of standard CA 152. The dose of the ethephon studied is 1000 g per hectare.

Trial 1 was carried out in December 1993 and Trial 2 in February 1994.

The results of Trial 1 are set out in Table II.

TABLE II

| | | Time of observation (in days) after treatment T | | | | | | | | |
|---|---|---|---|---|---|---|---|---|---|---|
| Products | Dose (g of ethephon/ha) | T + 2d | T + 3d | T + 4d | T + 5d | T + 6d | T + 7d | T + 8d | T + 9d | T + 10d |
| | | % of fallen petioles | | | | | | | | |
| Control | | 0 | 0 | 0 | 0 | 0 | 0 | 0 | 0 | 0 |
| CA152 | 1000 | 0 | 0 | 30 | 63 | 83 | 91 | 100 | | |
| LAB695 | 1000 | 0 | 0 | 50 | 76 | 91 | 96 | 98 | 100 | |
| LAB696 | 1000 | 0 | 4 | 46 | 80 | 91 | 100 | | | |
| LAB697 | 1000 | 0 | 11 | 59 | 89 | 100 | | | | |

In the case of the "Control", water is applied without an active ingredient.

The results of trial 2 are set out in Table III.

TABLE III

| Products | Dose (g of ethephon/ha) | Time of observation (in days) after treatment T ||||||||| 
|---|---|---|---|---|---|---|---|---|---|---|
| | | T + 2d | T + 3d | T + 4d | T + 5d | T + 6d | T + 7d | T + 8d | T + 9d | T + 10d |
| | | % of fallen petioles ||||||||| 
| Control | | 0 | 0 | 0 | 0 | 0 | 0 | 0 | 0 | 0 |
| CA152 | 1000 | 0 | 0 | 0 | 0 | 12 | 41 | 62 | 65 | 82 |
| LAB695 | 1000 | 0 | 0 | 0 | 9 | 24 | 68 | 79 | 88 | 94 |
| LAB696 | 1000 | 0 | 0 | 0 | 18 | 35 | 76 | 97 | 100 | |
| LAB697 | 1000 | 0 | 0 | 0 | 15 | 56 | 91 | 94 | 97 | 100 |

On examination of the results set out in Tables I and II it is noted that the abscission kinetics differ from one product to another; the absence of leaf-fall in the batches of control plants shows that the differences observed are indeed inherent in the differences of activity between products;

the compositions according to the invention are clearly distinguished from the standard by the following points:
→ the petiol fall starts earlier after application,
→ once started, the number of petioles which fall per unit of time is greater; therefore, at a given observation date after abscission has started, the level of effectiveness is clearly greater (on the third day from starting it is of the order of +20 to +30% in the first trial and of the order of 30 to +50% in the second).

These results show that the ethylenic activity of the compositions based on ethephon according to the invention is exhibited much more rapidly than that of the standard and that the level of effectiveness which they attain is generally greater.

b) Series of Trials 3 to 6

This series of four trials was carried out using the composition LAB 697; its purpose is to confirm the results of the first series.

Trials 3 to 6 were carried out respectively in October 1994, for Trials 3 and 4, in June 1994, for Trial 5 and in May 1994, for Trial 6.

In Trials 3 and 4, the dose studies was 750 g of ethephon/ha.

In Trials 5 and 6, it was 1000 g of ethephon/ha.

The results of Trials 3 to 6 are presented in Tables IV to VII respectively.

TABLE IV

| Products | Dose (g of ethephon/ha) | Time of observation (in days) after treatment T ||||||||| 
|---|---|---|---|---|---|---|---|---|---|---|
| | | T + 2d | T + 3d | T + 4d | T + 5d | T + 6d | T + 7d | T + 8d | T + 9d | T + 10d |
| | | % of fallen petioles ||||||||| 
| Control | | 0 | 0 | 0 | 0 | 0 | 0 | 0 | 0 | 0 |
| CA152 | 750 | 0 | 0 | 2 | 23 | 67 | 90 | 96 | 98 | 100 |
| LAB697 | 750 | 0 | 0 | 15 | 54 | 87 | 94 | 96 | 98 | 100 |

TABLE V

| Products | Dose (g of ethephon/ha) | Time of observation (in days) after treatment T ||||||||| 
|---|---|---|---|---|---|---|---|---|---|---|
| | | T + 2d | T + 3d | T + 4d | T + 5d | T + 6d | T + 7d | T + 8d | T + 9d | T + 10d |
| | | % of fallen petioles ||||||||| 
| Control | | 0 | 0 | 0 | 0 | 0 | 0 | 0 | 0 | 0 |
| CA152 | 750 | 0 | 0 | 2 | 54 | 78 | 91 | 96 | 100 | |
| LAB697 | 750 | 0 | 4 | 28 | 83 | 98 | 100 | | | |

TABLE VI

| Products | Dose (g of ethephon/ha) | T + 2d | T + 3d | T + 4d | T + 5d | T + 6d | T + 7d | T + 8d | T + 9d | T + 10d |
|---|---|---|---|---|---|---|---|---|---|---|
| | | | | | % of fallen petioles | | | | | |
| Control | | 0 | 0 | 0 | 0 | 0 | 0 | 0 | 0 | 0 |
| CA152 | 1000 | 0 | 16 | 87 | 97 | 97 | 100 | | | |
| LAB697 | 1000 | 3 | 67 | 100 | | | | | | |

TABLE VII

| Products | Dose (g of ethephon/ha) | T + 2d | T + 3d | T + 4d | T + 5d | T + 6d | T + 7d | T + 8d | T + 9d | T + 10d |
|---|---|---|---|---|---|---|---|---|---|---|
| | | | | | % of fallen petioles | | | | | |
| Control | | 0 | 0 | 0 | 0 | 0 | 0 | 0 | 0 | 0 |
| CA152 | 1000 | 0 | 0 | 0 | 0 | 11 | 31 | 47 | 56 | 64 |
| LAB697 | 1000 | 0 | 3 | 33 | 67 | 72 | 92 | 97 | 97 | 97 |

Examination of the results set out in Tables IV to VII allows the following conclusions to be drawn.

These results:

confirm that the concomitant use of adjuvants and ethephon allows a more rapid and more intense response of plants than ethephon alone, suggests a lower sensitivity of the proposed specialities to cultivation conditions; in fact, whilst the standard does not achieve the expected result in Trial 6, the use of the products according to the invention allows a very satisfactory level of effectiveness to be achieved.

3. Biological Trials as a Field Crop (on Field)

The effectiveness of the "adjuvants" used concomitantly with ethephon is studied in the application for the defoliation of cotton (Stoneville variety) cultivated as a field crop in farmers' plots.

The study is illustrated by Trials 7 and 8. Their location and their characteristics are specified in Table VIII.

TABLE VIII

| Trials | 7 | 8 |
|---|---|---|
| Location | Coria del Rio Seville, Spain | Torre de la reina Seville, Spain |
| Date of treatment | 19/09/94 | 13/10/94 |
| T° max | 27° C. | 31° |
| T° min | 19° C. | 22° C. |
| Volume of plant protection mixture | 500 l/ha | 500 l/ha |

The trials are carried out according to a layout in blocks of 3 replicates including the control. The basic plots are 32 m² (4 rows of 8 m in length).

The composition LAB 697 was studied in comparison to the standard (Ethrel® 48 or CA 152). Each product is applied at the dose of 1200 g of ethephon/ha.

The visual percentage of defoliation of the cotton is evaluated when the trials are set up, then after treatment regularly every 3 days.

The results of Trials 7 and 8 are set out respectively in Tables IX and X hereafter.

TABLE IX (the results are the average of 3 repeats)

| Products | Dose (g of ethephon/ha) | T | T + 3d | T + 6d | T + 9d |
|---|---|---|---|---|---|
| | | | | % defoliation | |
| Control | | 6.2 | 16.7 | 52.5 | 57.5 |
| CA152 | 1200 | 7.5 | 27.5 | 65.8 | 78.3 |
| LAB697 | 1200 | 6.7 | 33.3 | 76.7 | 85 |

TABLE X (the results are the average of 3 repeats)

| Products | Dose (g of ethephon/ha) | T | T + 3d | T + 6d | T + 9d |
|---|---|---|---|---|---|
| | | | | % defoliation | |
| Control | | 5 | | 7.5 | 45 |
| CA152 | 1200 | 7.5 | | 21.7 | 69.2 |
| LAB697 | 1200 | 7.5 | | 26.7 | 80.8 |

Examination of the results set out in Tables IX and X allows it to be noted that, if ethephon alone intensifies the defoliation of cotton relative to the untreated control, the concomitant use of "adjuvants" or products used in accordance with the invention allow a clearly more marked activity to be obtained.

More generally, the observations made both in the greenhouse and in field crops allow the importance of the process and compositions according to the invention to be stated from three points of view:

a) the active ingredient is better enhanced and
   a better level of effectiveness can be obtained for the same quantity of ethephon,
   the quantity of ethephon applied can be reduced for a given expected effect, resulting in a lesser operating cost and a better respect for the environment,
b) the reduction in time between the treatment and the response allows the decision to apply the product to be taken with the shortest of delays, which increases the flexibility of use, c) the lower sensitivity noted for the product as regards climatic condition extends the times of the year when the product can be used.

We claim:

1. Ethephon-based composition for the regulation on plant growth containing, in addition to ethephon at least one product or adjuvant the chemical structure of which contains at least two acid functions selected from the group comprising acid functions of carboxylic type of formula (—COOH) and acid functions of phosphonic type of formula (—PO$_3$H$_2$), at least one of these acid functions being the (—PO$_3$H$_2$) function, said product being selected from the group comprising that having the formula

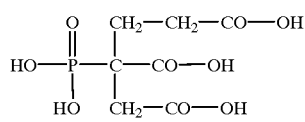

and those in which the functions are connected
by an organic chain of (—R—O—R) type containing an ether function wherein the two chains R are identical to or different from each other.
and/or an organic chain of (—R—NH—R) type containing a secondary amine function wherein the two chains R are identical to or different from each other, and/or an organic of

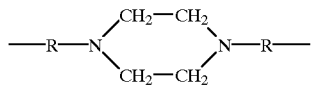

type containing two tertiary amine functions wherein the two chains R are identical to or different from each other,
and/or by a chain of

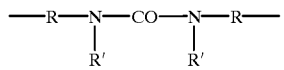

type in which (—R') represents hydrogen or the afore-mentioned chain R,
and/or by an organic chain of

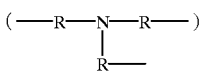

type containing a tertiary amine function wherein the three chains R are identical to or different from each other, wherein R represents a linear or branched hydrocarbon chain containing from 2 to 6 carbon atoms and optionally one or more substituents of hydroxyl type (—OH) and/or halogen and/or hydroxethyl (—CH$_2$—CH$_2$—OH) and/or phenyl (—C$_6$H$_5$) and/or hydroxyphenyl (—C$_6$H$_4$—OH).

2. Composition according to claim 1, characterized in that the chemical structure of the product or adjuvant which contains at least two acid functions, is represented by one of the general formulae indicated hereafter:

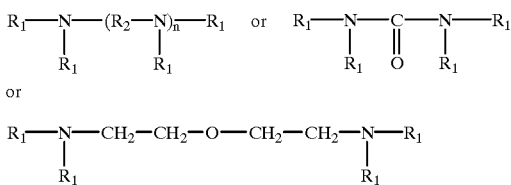

or

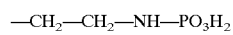

in which n represents an integer from 0 to 4,

R$_2$ represents a linear or branched hydrocarbon group having 2 to 6 carbon atoms, R$_1$ represents, independently at each occurrence, a hydrogen atom, an alkyl chain having 1 to 4 carbon atoms, a phenyl group, a hydroxyphenyl group, a hydroxyalkyl group, an alkylene-phosphonic acid group or one of the five groups represented below:

—CH$_2$—CH$_2$—NH—PO$_3$H$_2$

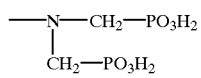

—CH$_2$—COOH  (the number of —CH$_2$—COOH groups being at most three)

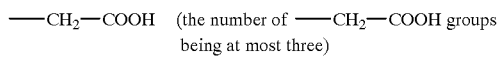
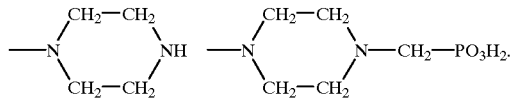

3. Composition according to claim 1, characterized in that the chemical structure of the product or adjuvant, which contains at least two acid functions, is represented by the formula

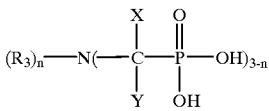

in which n represents an integer equal to 0 or 1,

X and Y represent a hydrogen atom or an alkyl group having 1 to 6 carbon atoms,

R$_3$ represents a hydrogen atom, an aliphatic hydrocarbon group, a halo-substituted aliphatic hydrocarbon group, a hydroxy-substituted aliphatic hydrocarbon group, the —CH$_2$COOH group or the

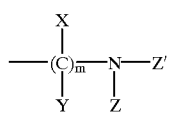

group in which m represents an integer from 1 to 6,

X and Y represent a hydrogen atom or an alkyl group,

Z represents a hydrogen atom or the

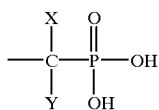

Z' represents Z or the group of formula

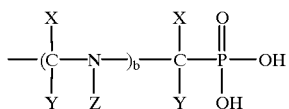

in which b is an integer from 1 to 6.

4. Composition according to claim 1, characterized in that the chemical structure of the product or adjuvant, which contains at least two acid functions, is represented by the formula

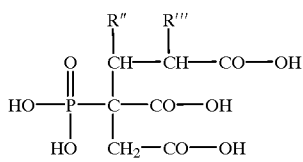

in which

R" represents hydrogen or a short alkyl chain having 1 to 4 carbon atoms,

R'" represents hydrogen or a methyl group, the products corresponding to formulae

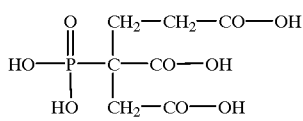

as well as

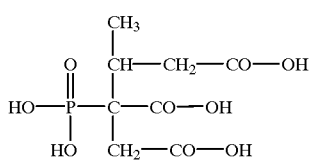

and

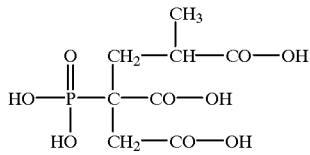

being more particularly preferred.

5. Composition according to claim 1, characterized in that the chemical structure of the product or adjuvant, which contains at least two acid functions, is represented either by the formula

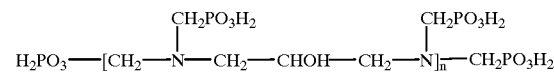

in which n is an integer from 1 to 5, or by the following products:

1,6-hexylenediamine-N,N,N',N'tetrakis((methylene)-phosphonic) acid, ethylenediamine-N,N,N',N'-tetrakis((methylene)-phosphonic) acid, diethylenetriamine-N,N,N',N",N"-penta((methylene)-phosphonic) acid, nitrilo-N,N,N-tris((methylene)-phosphonic) acid which are particularly preferred.

6. Composition according to claim 1, characterized in that the chemical structure of the product or adjuvant, which contains at least two acid functions, is represented by one of the formulae

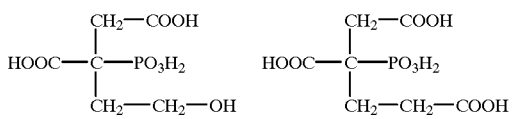

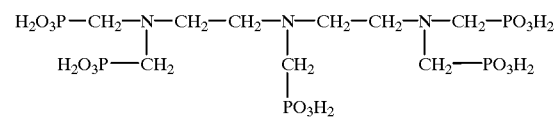

and

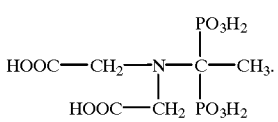

7. Composition according to one of claims 1 and 2 to 6, characterized in that the ratio of ethephon/adjuvant by weight is 10/1 to 1/10, preferably 5/1 to 1/5.

8. Plant growth regulation process comprising applying, on the plants to be treated, ethephon and at least one product, the chemical structure of which is characterized in that it contains at least two acid functions selected from the group comprising acid functions of carboxylic type of formula (—COOH) and acid functions of phosphonic type of formula (—PO$_3$H$_2$), at least one of these acid functions being the (—PO$_3$H$_2$) function, said product being selected from the group comprising that having the formula:

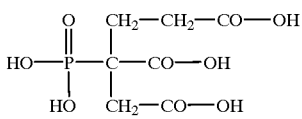

and those in which the acid functions are connected
by an organic chain of (—R—O—R) type containing an ether function wherein the two chains R are identical to or different from each other,
and/or an organic chain of (—R—NH—R) type containing a secondary amine function wherein the two chains R are identical to or different from each other, and/or an organic chain of

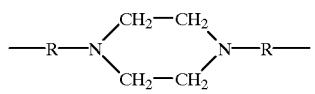

type containing two tertiary amine functions wherein the two chains R are identical to or different from each other,
and/or by a chain of

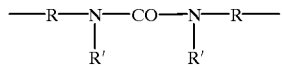

type in which (—R') represents hydrogen or the aforementioned chain R,
and/or by an organic chain of

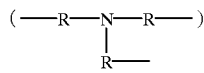

type containing a tertiary amine function wherein the three chains R are identical to or different from each other, wherein R represents a linear or branched hydrocarbon chain containing from 2 to 6 carbon atoms and optionally one or more substituents of hydroxyl type (—OH) and/or halogen and/or hydroxyethyl (—CH$_2$—CH$_2$—OH) and/or phenyl (—C$_6$H$_5$) and/or hydroxyphenyl (—C$_6$H$_4$—OH).

9. Process according to claim 8, characterized in that 20 g to 3000 g of ethephon and 20 g to 5000 g of one or more adjuvants according to one of claims 1 and 2 to 6 are applied per hectare.

10. Process for plant growth regulation characterized in that an effective quantity is applied to the plants to be treated depending on the cultivation, the physiological stage and the effect sought, preferably from 20 to 3000 g of ethephon and preferably 20to 5000 g of one or more adjuvants according to one of claims 1 and 2 to 6.

11. Process according to claim 10, characterized in that the composition is preferably applied in the form of a plant protection mixture containing 20 g to 3000 g of ethephon and 20 to 5000 g of adjuvant according to one of claims 1 and 2 to 7, the whole being dissolved in 20 to 3000 litres of water.

* * * * *